(12) United States Patent  
Hooper et al.

(10) Patent No.: US 8,057,748 B2  
(45) Date of Patent: Nov. 15, 2011

(54) SYRINGE, SYSTEM AND METHOD FOR DELIVERING OXYGEN-OZONE

(75) Inventors: David M. Hooper, Austin, TX (US); Thomas Foster, Boulder, CO (US); Noel Henson, Valley, WA (US)

(73) Assignee: Minimus Spine, Inc., Austin, TX (US)

( * ) Notice: Subject to any disclaimer, the term of this patent is extended or adjusted under 35 U.S.C. 154(b) by 1056 days.

(21) Appl. No.: 11/976,362

(22) Filed: Oct. 24, 2007

(65) Prior Publication Data

US 2009/0110614 A1   Apr. 30, 2009

(51) Int. Cl.  
*B01J 19/08* (2006.01)

(52) U.S. Cl. .............. 422/186.07; 204/176; 604/25; 96/108; D24/114

(58) Field of Classification Search .......... 422/186.07; 204/176; 604/25; 96/108; D24/114  
See application file for complete search history.

(56) References Cited

U.S. PATENT DOCUMENTS

| | | | |
|---|---|---|---|
| 4,725,412 A | 2/1988 | Ito | |
| 5,052,382 A | 10/1991 | Wainwright | |
| 5,503,809 A * | 4/1996 | Coate et al. ............... 422/186.18 |
| 5,540,898 A | 7/1996 | Davidson | |
| 6,007,785 A | 12/1999 | Liou | |
| 6,110,431 A | 8/2000 | Dunder | |
| 6,270,733 B1 | 8/2001 | Rodden | |
| 6,331,279 B1 | 12/2001 | Martin | |
| 6,601,602 B2 | 8/2003 | Adler et al. | |
| 6,679,419 B1 | 1/2004 | Sarracino | |
| 2003/0165411 A1 | 9/2003 | Engelhard | |
| 2005/0074501 A1 | 4/2005 | Murphy et al. | |
| 2007/0025890 A1 | 2/2007 | Joshi et al. | |
| 2007/0154363 A1 * | 7/2007 | Joshi et al. ............... 422/186.04 |

FOREIGN PATENT DOCUMENTS

| | | |
|---|---|---|
| DE | 447 936 | 7/1927 |
| DE | 3119581 A1 | 12/1982 |
| KR | 100489636 | 5/2005 |

OTHER PUBLICATIONS

International Search Report dated Mar. 27, 2009 to corresponding international application No. PCT/US2008/012026.

* cited by examiner

*Primary Examiner* — Jeffrey T Barton  
*Assistant Examiner* — Xiuyu Tai  
(74) *Attorney, Agent, or Firm* — Maier & Maier, PLLC (57) ABSTRACT

In accordance with at least one exemplary embodiment, a syringe, method and system for delivering a therapeutic amount of ozone are disclosed. An exemplary syringe can have a gas chamber and one or more electrodes. A portion of at least one electrode can be within the gas chamber. Alternatively, singularly or in conjunction, one or both electrodes can be attached to the outside of an exemplary syringe. One or more electrical contact points can be outside the gas chamber. Each electrical contact point can be connected to an electrode. Oxygen gas can provided within the gas chamber of the exemplary syringe. A medical ozone generator can be connected to the syringe via the electrical contact points. Corona discharge can be effectuated via the electrodes, which can result in an amount of ozone gas can being produced from the oxygen gas.

3 Claims, 12 Drawing Sheets

SYRINGE, SYSTEM AND METHOD FOR DELIVERING OXYGEN-OZONE

BACKGROUND

Ozone is an unstable gas with a half-life of less than one hour at room temperature. Ozone is a powerful oxidizer. It is a known bactericide and viricide. Methods for converting oxygen to ozone involve high-voltage corona discharge or ultraviolet light. Ozone generators making use of such methods are available for industrial uses.

Ozone has a variety of industrial applications. Applications include deodorizing air, purifying water and sterilizing medical instruments, among others. Ozone and conventional medical ozone generators are being used therapeutically in many countries and have been so for several years. Such applications include, but are not limited to, autohemotherapy, rectal insufflations, intradiscal injection, injection into knee and shoulder joints, and full body exposure.

For example, ozone is used to treat diffuse bulging or contained herniation of the spinal disc. Spinal discs are composed of a fibrous outer ring made of Type I collagen and a softer more flexible nucleus made of Type II collagen, proteoglycans and water. Patients with disc bulging or herniation suffer from pain caused by disc compression of the neurological elements, including the spinal cord, cauda equina and nerve roots. Intradiscal ozone treatment involves direct injection of a gaseous mixture of oxygen and ozone into the nucleus of the disc. Ozone releases water from the proteoglycans, reducing disc size and relieving compression of neurological elements. Some investigators believe that ozone stimulates anti-inflammatory mediators and initiates a healing response.

The mechanism of action and reported success rates of ozone treatment for spinal disc herniation are comparable to that of the enzyme chymopapain. Chymopapain was first FDA-approved in 1983 and was widely used with a success rate of 65-85%. A small number of serious complications, including death and paralysis, caused the product to lose favor in the U.S. market.

Ozone and chymopapain are two means of performing a chemical discectomy through a needle puncture. This minimally invasive approach may be preferred to surgical discectomy, which requires general anesthesia and direct access to the spinal disc.

Therapeutic ozone must be delivered shortly after being produced from oxygen. Conventional medical ozone generators pass medical grade oxygen through an electric field or ultraviolet light. This process converts an amount of oxygen into ozone. Typically, a syringe is interfaced with the generator and ozone is withdrawn from a gas chamber of the generator into the syringe for subsequent injection therapy.

The preferred concentration of ozone for intradiscal injection is approximately 6%. The concentration of ozone is important for medical uses. If the concentration is too low, the treatment will not be effective. If the concentration of ozone is too high, detrimental effects may follow.

As such, medical ozone generators include a means for measuring the concentration of ozone. Conventional ozone generators also have means for controlling the concentration and delivery of ozone gas. For example, some generators include components that neutralize excess ozone. Other generators continuously vent ozone.

Conventional ozone generators typically include permanent and reusable electrodes. The gas chambers of conventional generators are often permanent and reusable as well. Reusable electrodes tend to degrade over time. Sterility is an issue for present ozone generators that pass oxygen through permanent and reusable gas chambers. To address such, medical professionals have been known to inject the gas through a bacterial filter.

SUMMARY

According to at least one exemplary embodiment, a cell for producing an amount of ozone from oxygen is disclosed. The cell can have a syringe, which can have a gas chamber. One or more electrodes can be attached to the syringe. One or more electrical contact points can be outside the gas chamber. Each electrical contact point can be connected to an electrode.

In another exemplary embodiment, a method of producing an amount of ozone from oxygen is disclosed. The method can include providing oxygen gas within a gas chamber of a syringe and effectuating a corona discharge from at least one electrode. The at least one electrode can be attached to the syringe. An amount of ozone gas can be produced from the oxygen gas.

In yet another exemplary embodiment, an ozone generation system is disclosed. The ozone generation system can include a syringe. The syringe can have a gas chamber. One or more electrodes can be attached to the syringe. The electrodes can be connected to electrical contact points. A medical ozone generator can be connected to the syringe via electrical contact points.

BRIEF DESCRIPTION OF THE FIGURES

Advantages of embodiments of the present invention will be apparent from the following detailed description of the exemplary embodiments thereof, which description should be considered in conjunction with the accompanying drawings in which.

DETAILED DESCRIPTION

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

The word "exemplary" is used herein to mean "serving as an example, instance, or illustration." Any embodiment described herein as "exemplary" is not necessarily to be construed as preferred or advantageous over other embodiments. Likewise, the terms "embodiments of the invention", "embodiment" or "invention" do not require that all embodiments of the invention include the discussed feature, advantage or mode of operation.

Referring to FIGS. 1A-1E, a syringe in accordance with at least one exemplary embodiment is shown. Syringe 100 can be single-use and may be reprocessable. Alternatively, syringe 100 may be multi-use with sterilization, although such embodiments would stray from current trends in healthcare. Syringe 100 can be fabricated, in whole or in part, by any conventional molding processes known to one having ordinary skill in the art. Syringe 100 can serve as a cell for producing an amount of ozone from oxygen when used with a suitable ozone conversion unit, as further described below. Syringe 100 can then be used to administer a therapeutic amount of ozone to a human or an animal as will be readily recognized by one having ordinary skill in the art.

Syringe 100 can include barrel 102, plunger 104 and gas chamber 106. Gas chamber 106 can be defined and bounded through the cooperation of barrel 102 and plunger 104. In at least one exemplary embodiment, syringe 100 can be sized to hold between 10 ml and 30 ml of fluid in gas chamber 106, including between 10 ml and 30 ml of medical grade oxygen.

Barrel 102 can be made of any suitable material that allows for at least some UV transmission. This can allow for the passage of a UV beam through barrel 102 and a gas within gas chamber 106 for measuring the concentration of ozone gas. Furthermore, barrel 102 can be constructed of any material that sufficiently balances the needs for ozone resistance and UV resistance while still allowing for suitable UV transmission for measuring the concentration of ozone. Flexibility in construction can be increased because syringe embodiments may only be exposed to ozone and UV light for a shortened/ decreased period of time.

For example, barrel 102 (in which, syringe 100, as a whole, can be constructed largely or wholly of the same) can be constructed of polyethylene, polytetraflouroethylene ("PTTF", TEFLON®), polyacrylate (acrylic polymers), polycarbonate, polystyrene, styrene copolymers, polypropylene and the like known to one having ordinary skill in the art. Barrel 102 can also be made of glass, as one more non-limiting example. In at least one exemplary embodiment, barrel 102 can be made of polyethylene even though polyethylene may only allow about 10% UV transmission. A UV transmission of about 10% can be enough to measure ozone concentration within gas chamber 106 with suitable accuracy.

Plunger 104 can be slidably engaged with a first open end (i.e. top end) of barrel 102. The engagement of plunger 104 with barrel 102 can define the bounds of gas chamber 106 within syringe 100. Through sliding movements of plunger 104 within barrel 102, a fluid, including a gaseous fluid (e.g., oxygen gas), can be drawn into and expelled from gas chamber 106. Plunger 104 can include a plunger head 108 on one end of plunger shaft 110. On the other end of plunger shaft 110 can be plunger piston 112. Plunger piston 112 can form a gas-tight seal with barrel 102. Plunger piston 112 may be made from or covered with rubber and the like known to one having ordinary skill in the art Tip portion 114 can extend in fluid communication from a second end of barrel 102 under the control of valve 116. Valve 116 can be a stopcock valve, as one non-limiting example. Connector 118 can be situated at the distal end of tip portion 114. Connector 118 can be a luer fitting (e.g., press-on or twist-on) and the like known to one having ordinary skill in the art. For example, connector 118 can be a luer lock fitting for receiving a hypodermic needle for use in an ozone therapy.

Wire electrodes 120, 122 can extend inwardly within barrel 102. In other embodiments, one or both electrodes may be disposed or retained on outer portions of syringe 100, as will be readily recognized by one having ordinary skill in the art. Wire electrodes 120, 122 may be made to extend inwardly by providing wire electrodes 120, 122 through barrel 102. Wire electrodes can be provided through barrel 102 in a gas-tight manner. Wire electrodes 120, 122 can be situated proximate the end of barrel 102 from which tip portion 114 can extend from. Placing wire electrodes 120, 122 towards the tip end (i.e. bottom end) of barrel 102 can assist or prevent plunger 104 and wire electrodes 120, 122 from interacting in a non-beneficial manner, such as causing damage to or misplacement of either, or compromising the gas-tight sealing functionality of plunger piston 112, leading to leakage. Wire electrodes 120, 122 can be made of any suitable conductive material known to one having ordinary skill in the art. Wire electrodes 120, 122 may be solid metal rods of a relatively simple construction, which may be cost-effective. In addition, a dielectric material may cover a portion(s) of wire electrode 120 and/or 122 in at least one exemplary embodiment.

Figure 1A:
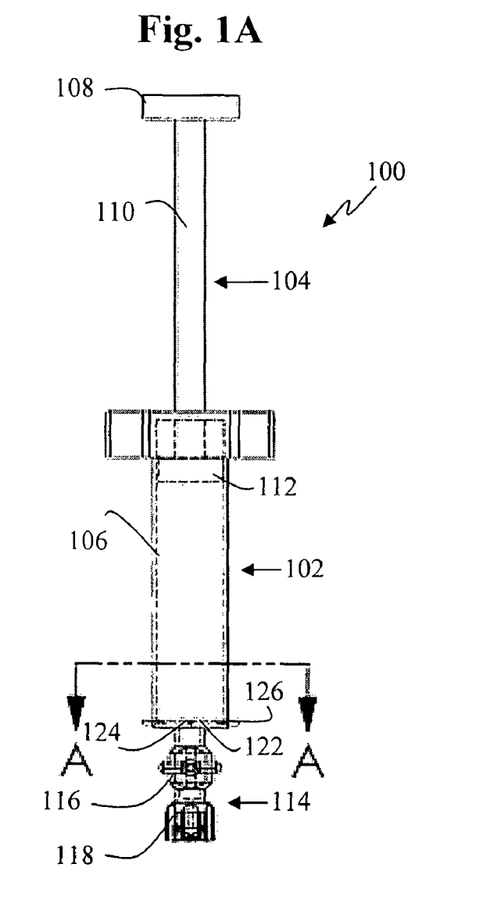
FIG. 1A is a side view of an exemplary syringe.
Figure 1B:
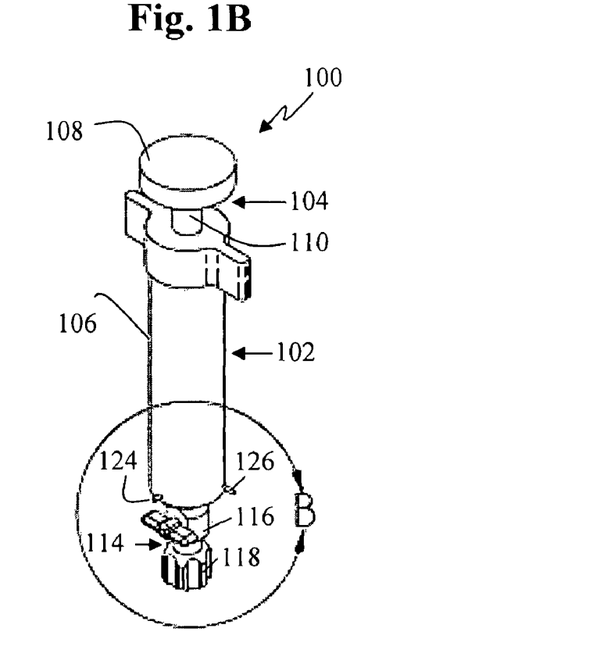
FIG. 1B is a perspective view of an exemplary syringe.
Figure 1C:
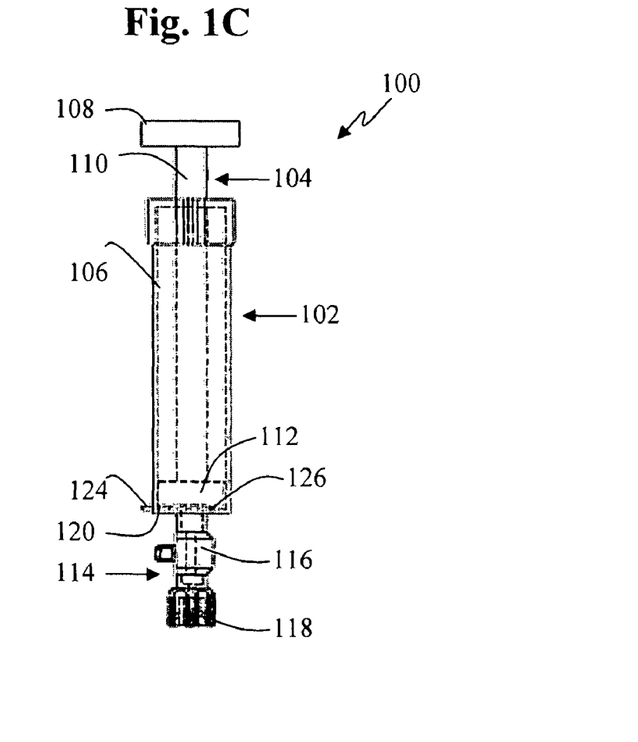
FIG. 1C is another side view of an exemplary syringe.
Figure 1D:
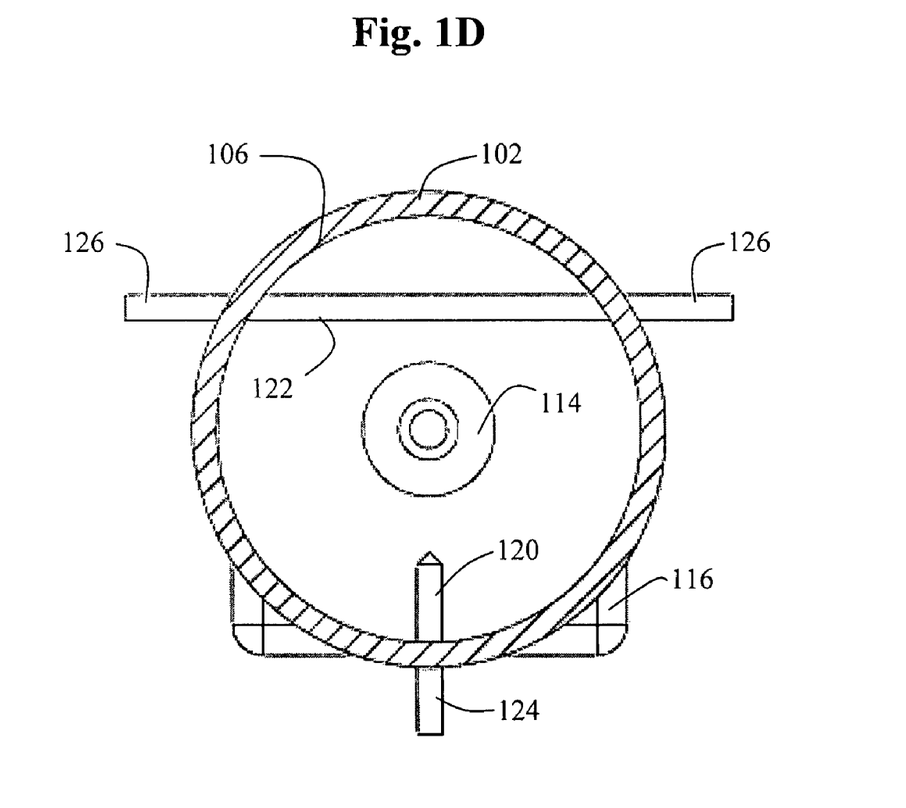
FIG. 1D is a cross-sectional view along line A of FIG. 1A.
Figure 1E:
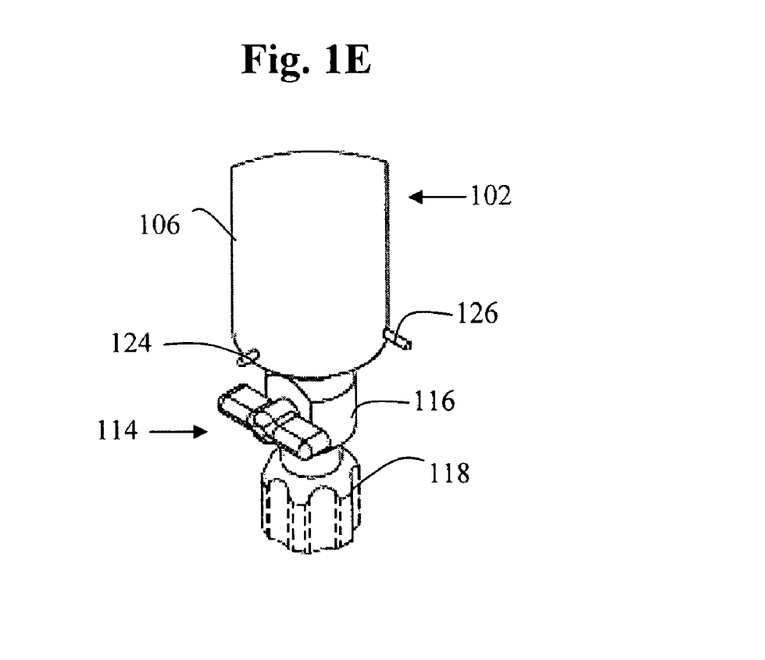
FIG. 1E is an enlarged view of the portion circumscribed by line B of FIG. 1B.
Figure 2A:
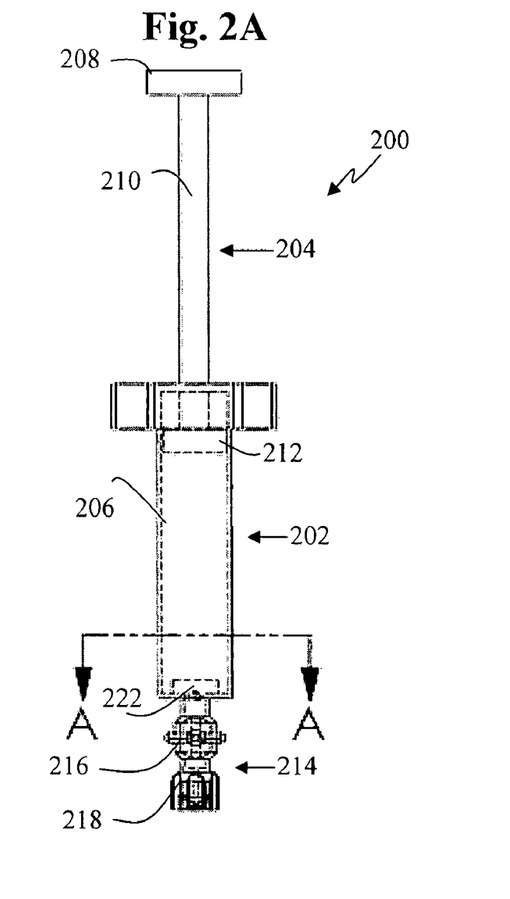
FIG. 2A is a side view of another exemplary syringe.
Figure 2B:
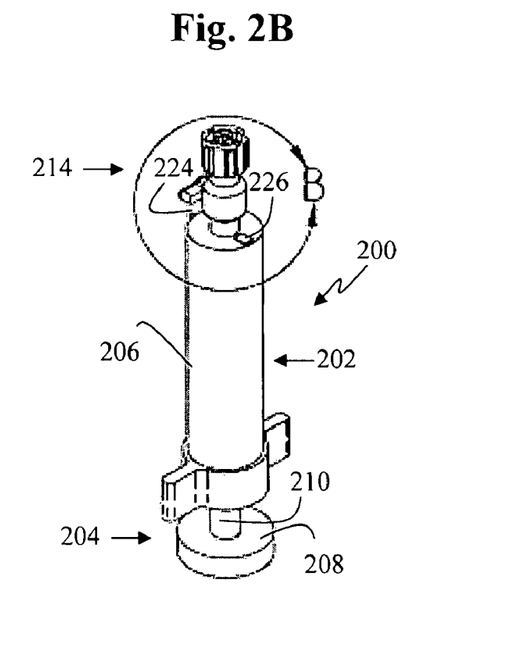
FIG. 2B is a perspective view of another exemplary syringe.
Figure 2C:
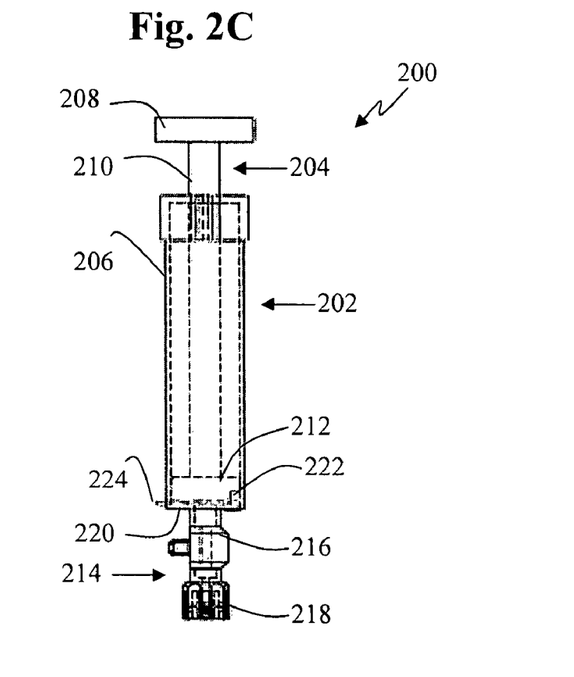
FIG. 2C is another side view of another exemplary syringe.
Figure 2D:
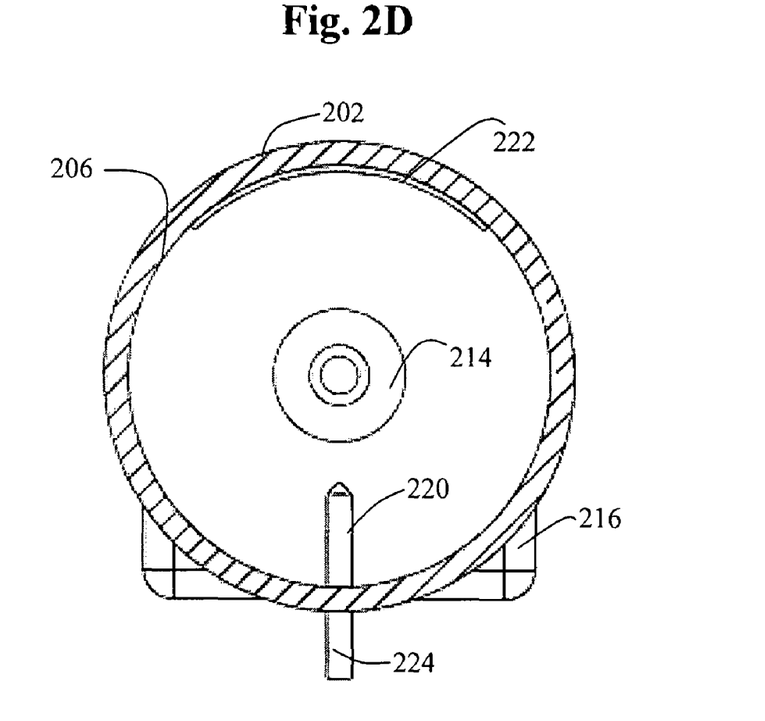
FIG. 2D is a cross-sectional view along line A of FIG. 2A.
Figure 2E:
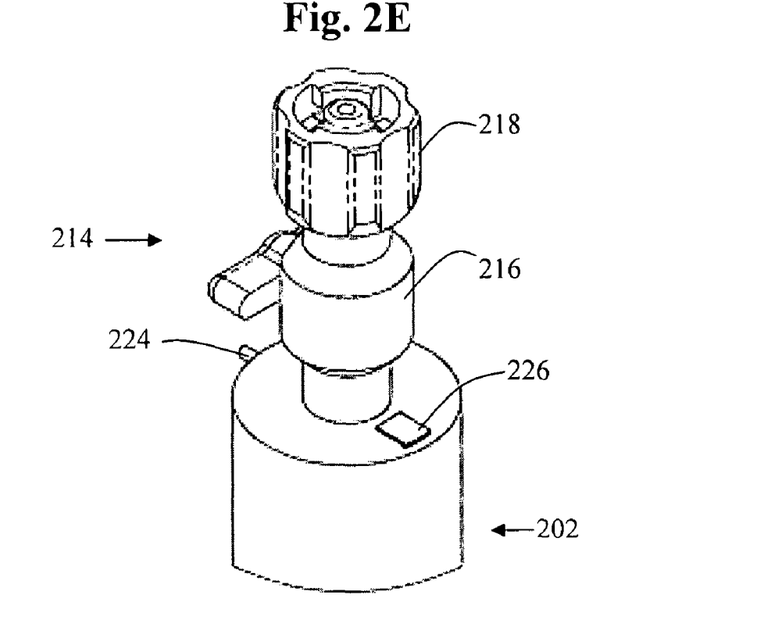
FIG. 2E is an enlarged view of the portion circumscribed by line B of FIG. 2B.
Figure 3A:
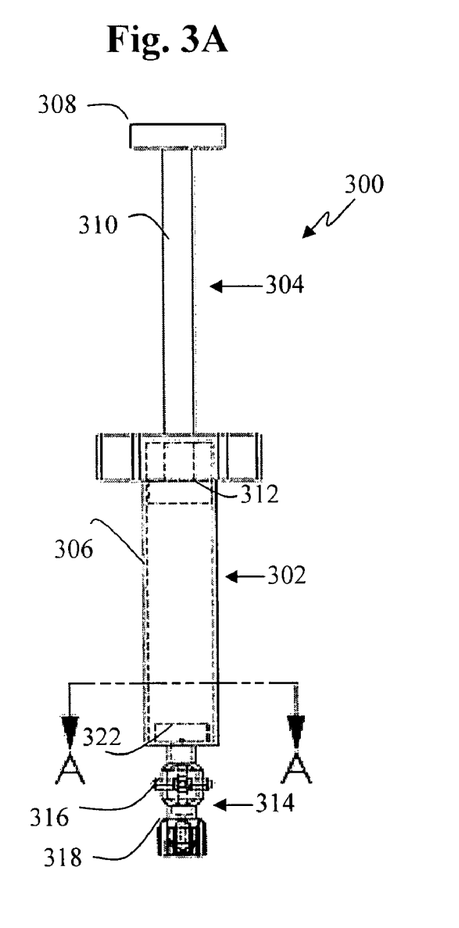
FIG. 3A is a side view of yet another exemplary syringe.
Figure 3B:
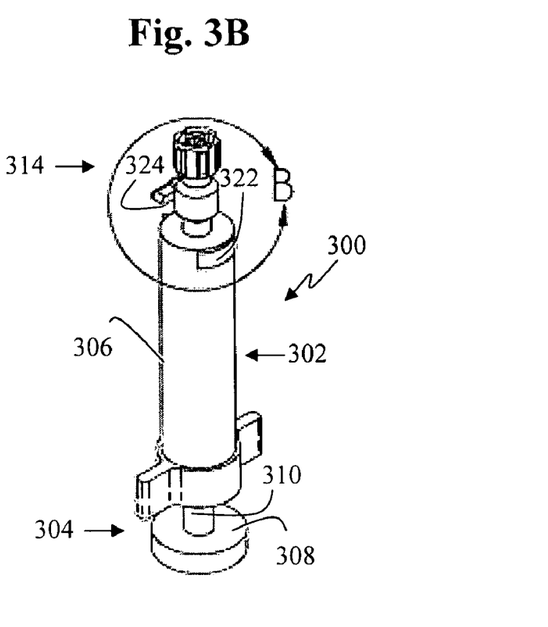
FIG. 3B is an inverted perspective view of yet another exemplary syringe.
Figure 3C:
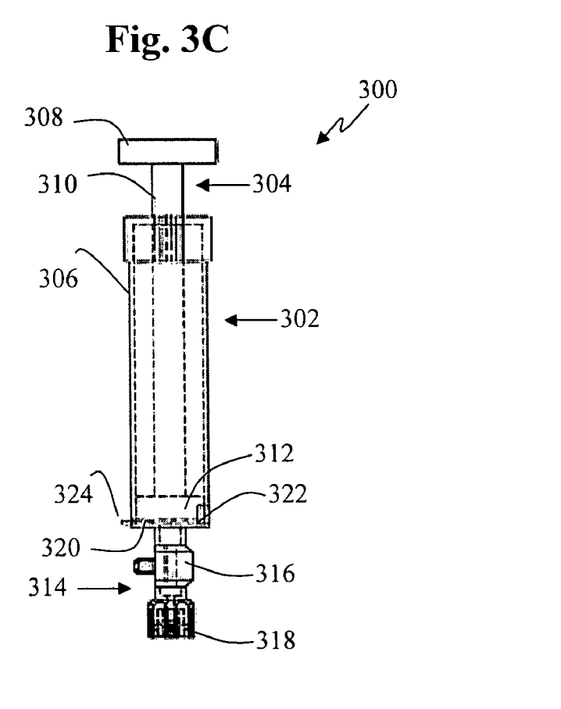
FIG. 3C is another side view of yet another exemplary syringe.
Figure 3D:
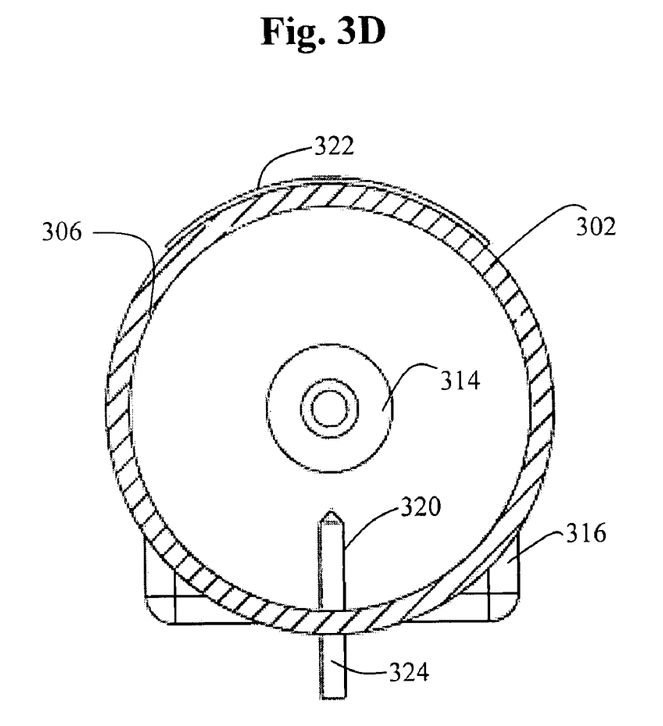
FIG. 3D is a cross-sectional view along line A of FIG. 3A.
Figure 3E:
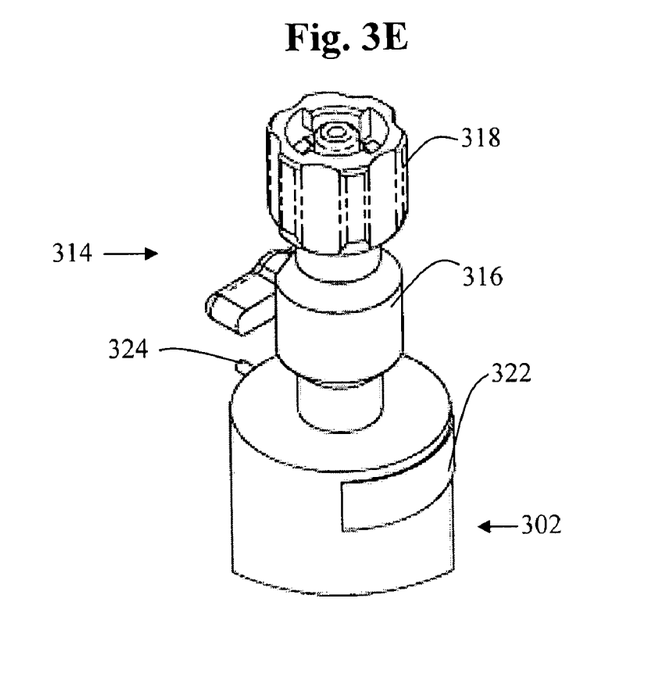
FIG. 3E is an enlarged inverted view of the portion circumscribed by line B of FIG. 3B.

Wire electrode 120 can extend inwardly towards the center of hollow barrel 102 (i.e. the center of gas chamber 106) as shown in cross-section. Wire electrode 120 may breach barrel 102 once and may retain a gas-tight seal proximate the breach. Wire electrode 120 can approach the center of gas chamber 106 in cross-section. Wire electrode 120 can be the discharge electrode. The end of wire electrode 120 situated within gas chamber 106 can form a sharp point. Alternatively, the end of wire electrode 120 can be blunt.

Wire electrode 122 can extend inwardly and can transverse a cross section of gas chamber 106. Wire electrode 122 can be straight (as shown) or can be curved. Wire electrode 122 may breach barrel 102 twice and may retain gas-tight seals proximate the breaches. Wire electrode 122 may transverse a cross section of gas chamber 106 off-center. Wire electrode 120 and wire electrode 122 can exist in a substantially perpendicular relationship without contacting one another. In other words, wire electrode 120 and wire electrode 122 can extend from and/or enter barrel 102 at approximately a right angle. Wire electrodes 120, 122 can also be disposed at substantially the same planar orientation in cross-section. Wire electrode 122 can be the ground electrode for completing a circuit and may be used to sustain the current flow.

Electrical contact points 124, 126 can be disposed on the outside of barrel 102, as well as various other positions as will be readily recognized to one having ordinary skill in the art. Electrical contact point 124 can be connected with wire electrode 120. Electrical contact point 124 may be an integral portion of wire electrode 120. Electrical contact points 126 can be disposed on opposite ends of wire electrode 122 outside of syringe 100. Electrical contact points 126 can be connected to wire electrode 122 and may be integral portions thereof.

Either or both of electrical contact points 126 and electrical contact point 124 can be connected to an ozone generation unit for effectuating a corona discharge via wire electrodes 120, 122. Wire electrode 120 can be the discharge electrode and wire electrode 122 can be the ground electrode. The corona discharge can be used to produce an amount of ozone from oxygen within gas chamber 106. A user can predetermine the amount (e.g., concentration) of ozone desired through operation of a suitable ozone conversion unit. For example, therapeutic levels for intradiscal injection may be up to 6% ozone by volume and such concentrations may be selected by a user of a suitable ozone conversion unit.

Referring to FIGS. 2A-2E, another syringe in accordance with at least one exemplary embodiment is shown. Similar to syringe 100 of FIGS. 1A-1E in construction and operation, syringe 200 can include barrel 202, plunger 204, gas chamber 206, plunger head 208, plunger shaft 210, plunger piston 212, tip portion 214, valve 216, connector 218, electrode 220, and electrical contact point 224. A redundant of description of like elements does not bear repeating here.

Foil electrode 222 can be disposed on a portion of the inner wall of barrel 202. Foil electrode 222 can be curved (as shown), for example, consistent with the curvature of the inner wall of barrel 202. Alternatively, foil electrode 222 can be linear. Foil electrode 222 can be relatively thin as is a known characteristic of foil electrodes in general. Foil electrode 222 can be situated towards the tip end (bottom end) of barrel 202. Nevertheless, foil electrode 222 can encompass an area of barrel 202 expected to contact plunger piston 212 of plunger 204 at certain times, when in use. The relatively thin nature of foil electrode 222 can hinder or prevent non-beneficial interaction between the two. Wire electrode 220 can extend towards and approach a face of foil electrode 222. Foil electrode 222 can be the ground electrode.

Electrical contact point 226 can be disposed on the outside of barrel 202, as well as various other positions as will be readily recognized by one having ordinary skill in the art. As shown, electrical contact point 226 can be situated on a bottom portion of barrel 202. Electrical contact point 226 can be connected to foil electrode 222. Electrical contact point 226 may be an integral portion of foil electrode 222. Electrical contact point 226 can be thicker or thinner then the remainder of foil electrode 222. Alternatively, foil electrode 222 and electrical contact point 226 can be of substantially the same thickness, which may vary.

Foil electrode 222 can be a one-piece insert having electrical contact point 226. Foil electrode 222 can breach barrel 202 so as to have a face on a portion of the wall of barrel 202 and the electrical contact point 226 on the outside of barrel 202. Foil electrode 222 can breach barrel 202 in a gas-tight manner.

Referring to FIGS. 3A-3E, yet another syringe in accordance with at least one exemplary embodiment is shown. Similar to syringe 100 of FIGS. 1A-1E in construction and operation, syringe 300 can include barrel 302, plunger 304, gas chamber 306, plunger head 308, plunger shaft 310, plunger piston 312, tip portion 314, valve 316, connector 318, electrode 320 and electrical contact point 324. A redundant of description of like elements does not bear repeating here.

Foil electrode 322 can be disposed on a portion of the outer wall of barrel 302. Foil electrode 322 can be attached to barrel 302 by any means known to one having ordinary skill in the art. As shown, foil electrode 332 can be situated proximate the bottom end (tip end) of barrel 302. Foil electrode 322 can be substantially the same size as the portion of foil electrode 222 of FIGS. 2A-2E within barrel 202 and can be likewise relatively thin. Alternatively, foil electrode 322 may be thicker. Because foil electrode 322 can be disposed outside of barrel 302, it is expected that it will have no effect on the operation of plunger 304. Wire electrode 320 can extend towards and approach a face of foil electrode 322 with a portion of barrel 302 interposed there between. Foil electrode 322 can be the ground electrode.

Referring to FIGS. 4A-4E, yet another syringe in accordance with at least one exemplary embodiment is shown. Similar to syringe 100 of FIGS. 1A-1E in construction and operation, syringe 400 can include barrel 402, plunger 404, gas chamber 406, plunger head 408, plunger shaft 410, plunger piston 412, tip portion 414, valve 416, connector 418, electrode 420 and electrical contact point 424. A redundant of description of like elements does not bear repeating here.

Syringe 400 can further include a second electrode 420 and a second electrical contact point 424 connected thereto. As one having ordinary skill in the art will readily recognize having the benefit of the above description of syringe 100 in conjunction with FIGS. 1A-1E, wire electrodes 420 can extend inwardly within barrel 402. Wire electrodes 420 may be made to extend inwardly by providing wire electrodes 420 through barrel 402. Wire electrodes can be provided through barrel 402 in a gas-tight manner. Wire electrode 420 can be situated proximate the bottom portion of barrel 402. Placing wire electrodes 420 towards the tip end (bottom end) of barrel 402 can assist in preventing plunger 404 and wire electrodes 420 from interacting in a non-beneficial manner, such as causing damage to or misplacement of either, or compromising the gas-tight functionality of plunger piston 412, leading to leakage. Wire electrodes 420 may also act as a stopper for plunger 404, although such contact may be undesirable.

Figure 4A:
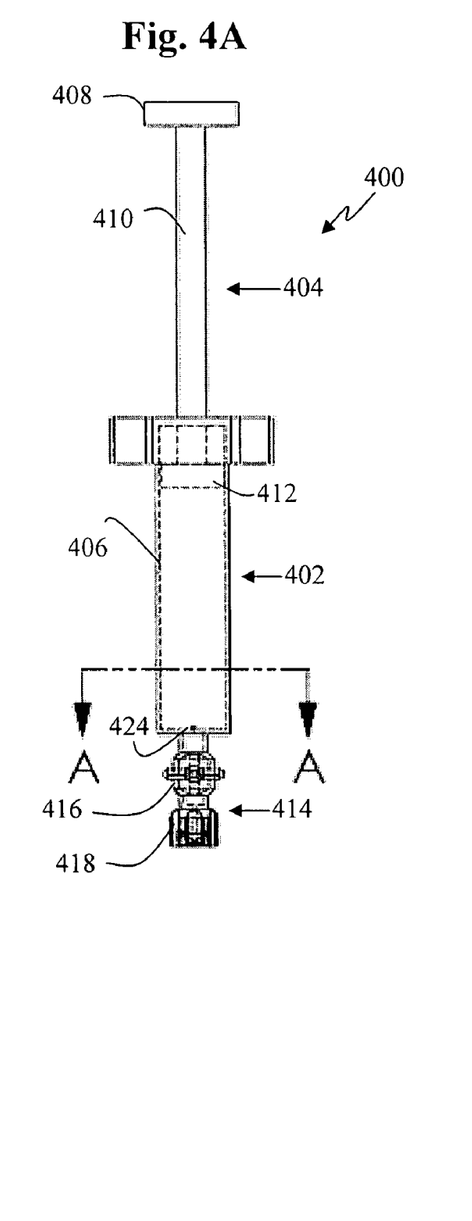
FIG. 4A is a side view of still another exemplary syringe.
Figure 4B:
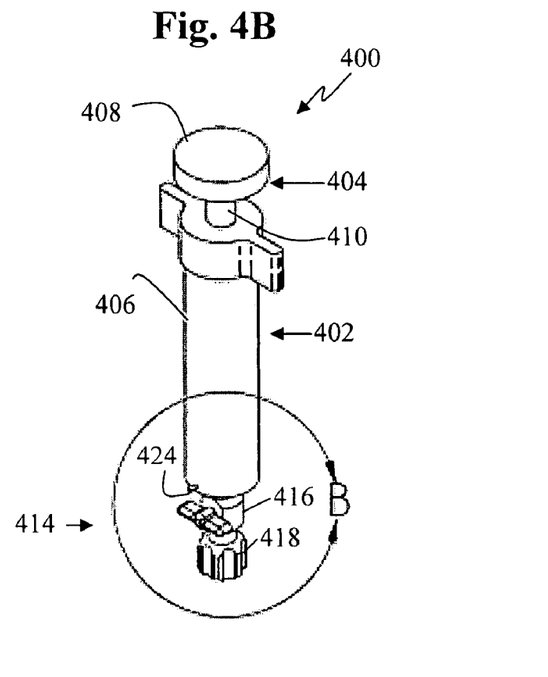
FIG. 4B is an inverted perspective view of still another exemplary syringe.
Figure 4C:
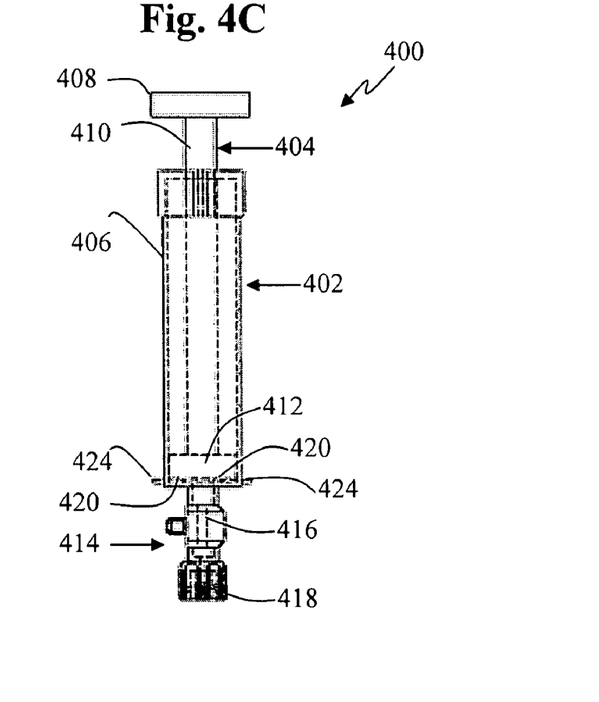
FIG. 4C is another side view of still another exemplary syringe.
Figure 4D:
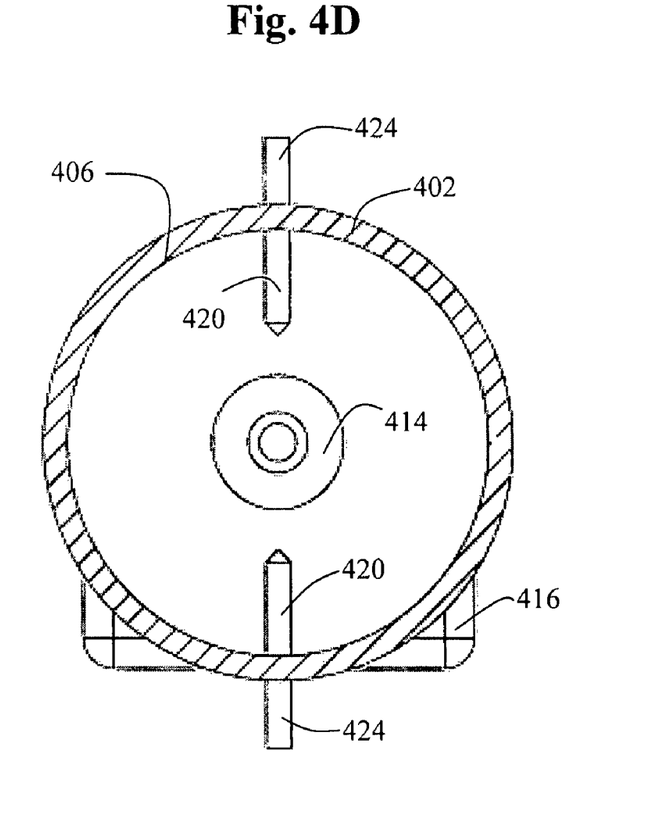
FIG. 4D is a cross-sectional view along line A of FIG. 4A.
Figure 4E:
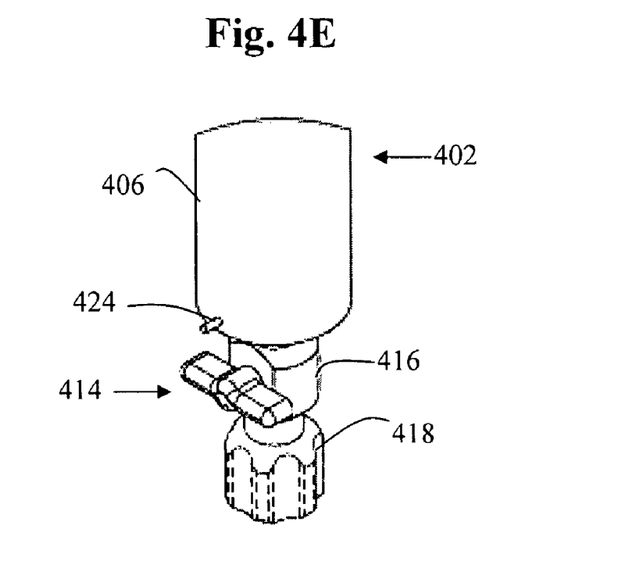
FIG. 4E is an enlarged inverted view of the portion circumscribed by line B of FIG. 4B.
Figure 5A:
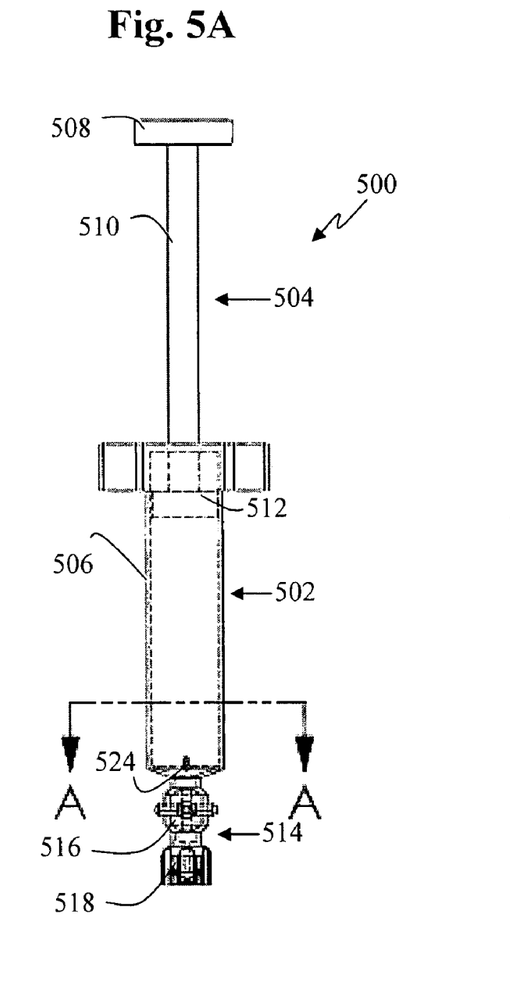
FIG. 5A is a side view of a further exemplary syringe.
Figure 5B:
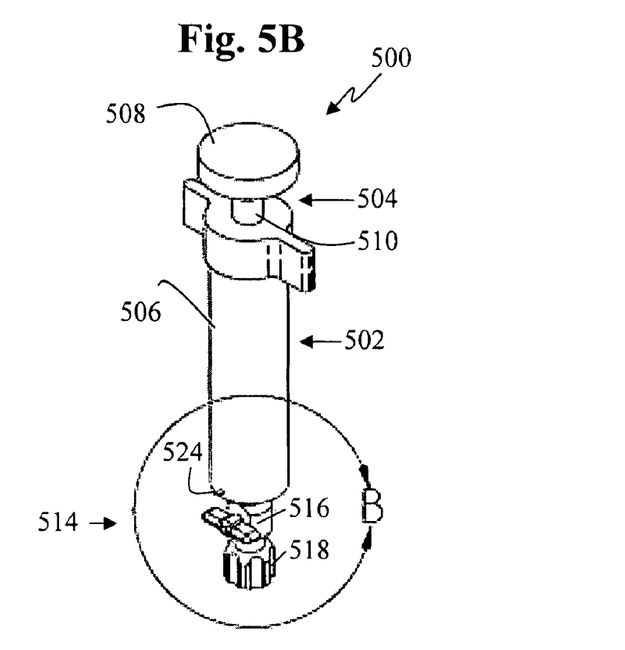
FIG. 5B is a perspective view of a further exemplary syringe.
Figure 5C:
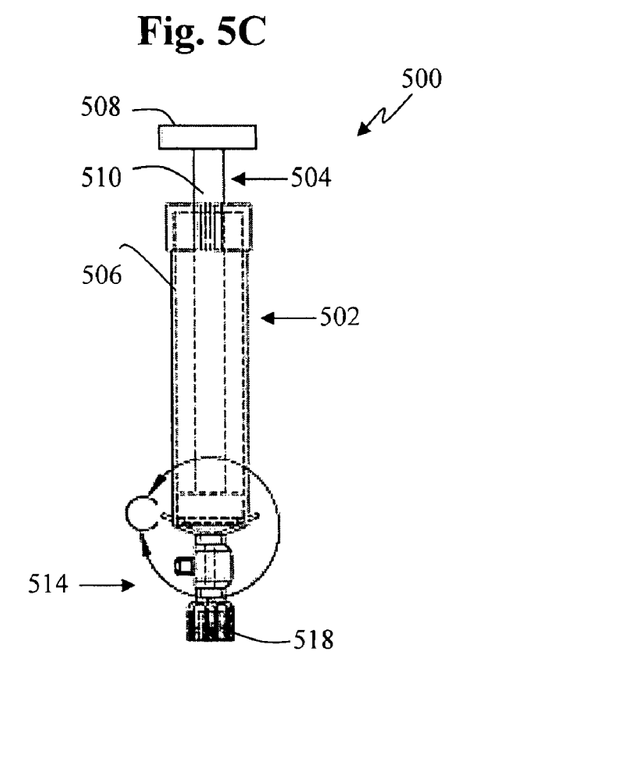
FIG. 5C is another side view of a further exemplary syringe.
Figure 5D:
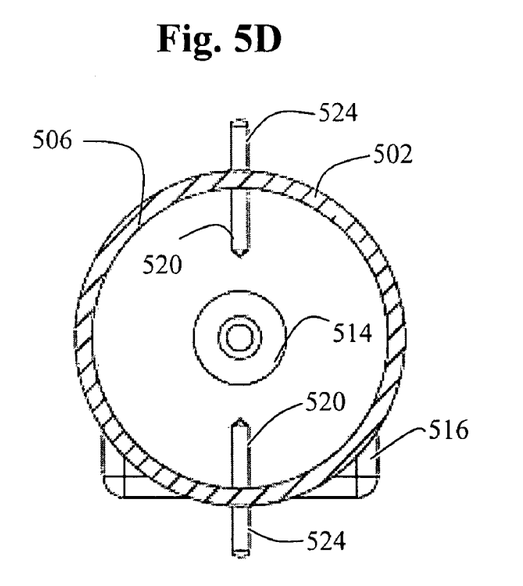
FIG. 5D is a cross-sectional view along line A of FIG. 5A.
Figure 5E:
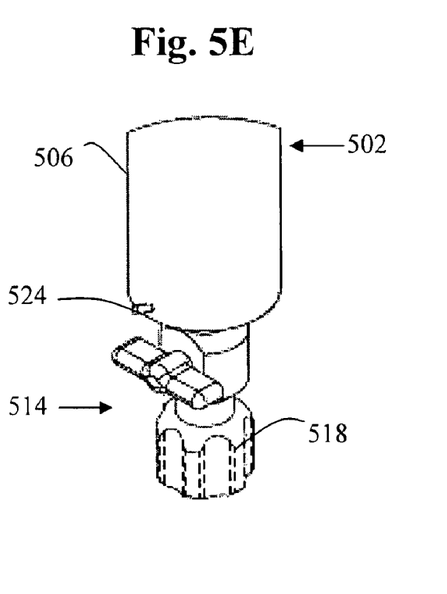
FIG. 5E is an enlarged view of the portion circumscribed by line B of FIG. 5B.
Figure 5F:
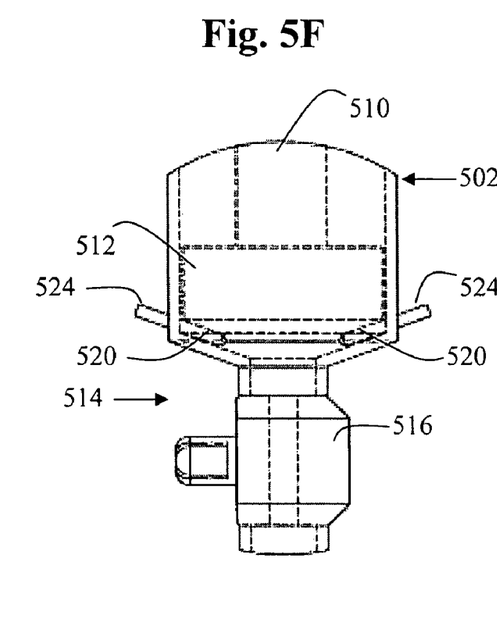
FIG. 5F is an enlarged view of the portion circumscribed by line C of FIG. 5C.
Figure 6A:
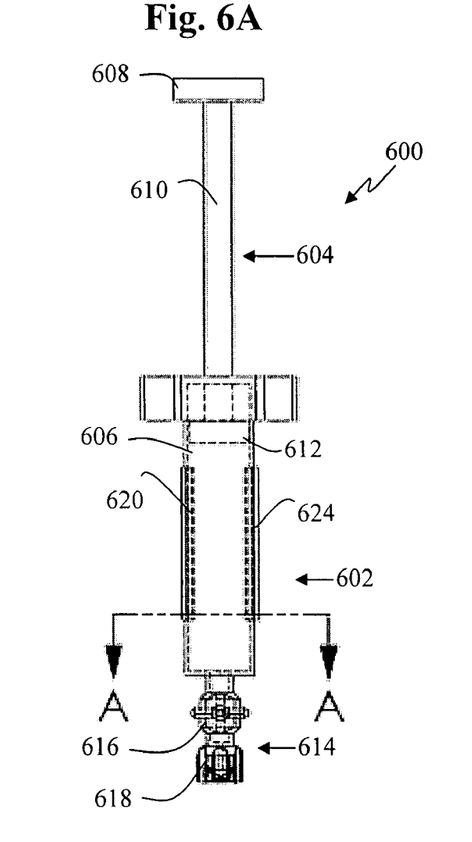
FIG. 6A is a side view of still a further exemplary syringe.
Figure 6B:
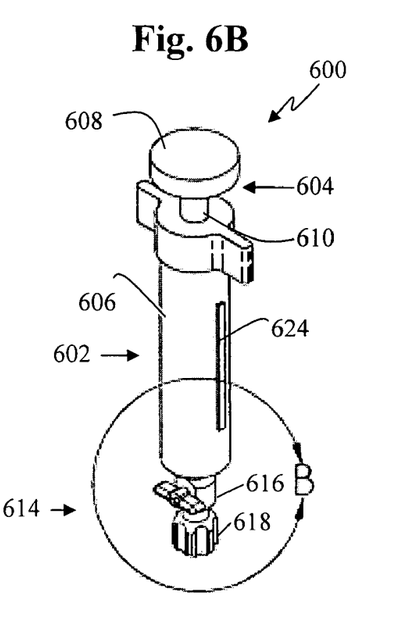
FIG. 6B is a perspective view of still a further exemplary syringe.
Figure 6C:
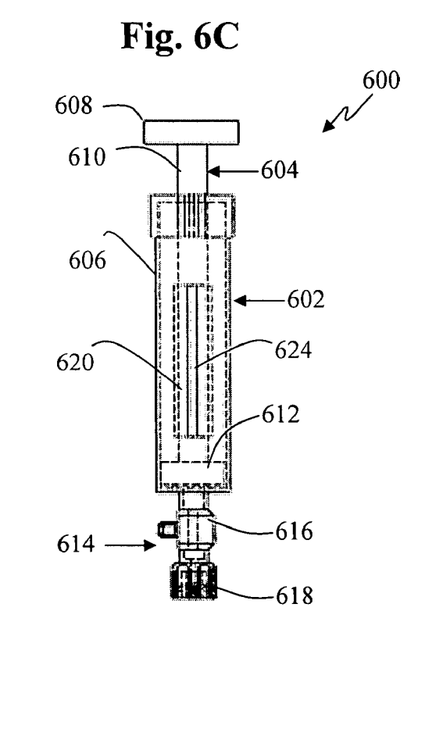
FIG. 6C is another side view of still a further exemplary syringe.
Figure 6D:
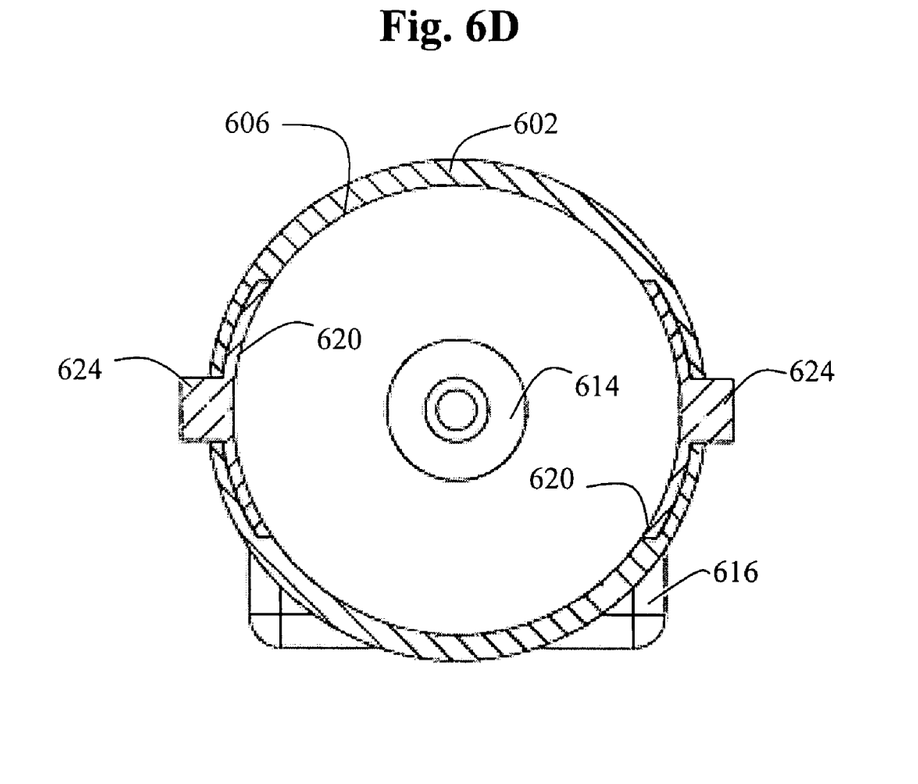
FIG. 6D is a cross-sectional view along line A of FIG. 6A.
Figure 6E:
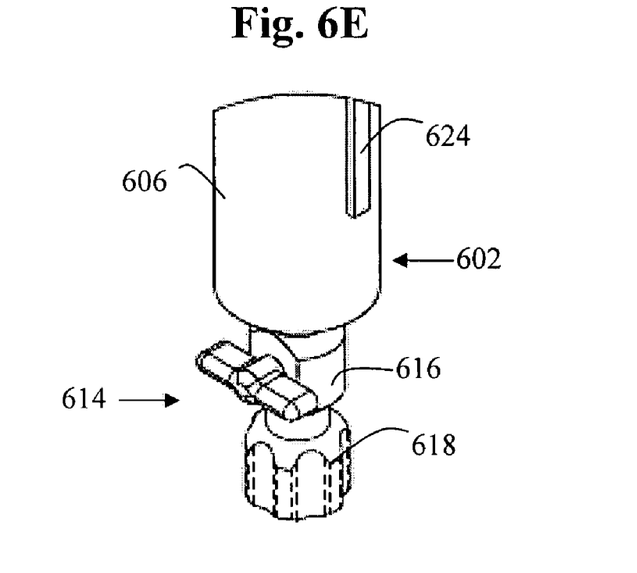
FIG. 6E is an enlarged view of the portion circumscribed by line B of FIG. 6B.

Wire electrodes 420 can extend inwardly towards the center of hollow barrel 402 as shown in cross-section. Wire electrodes 420 can approach the center of gas chamber 406 in cross-section. Wire electrodes 420 can exist in a substantially opposing relationship without contacting one another. Wire electrodes 420 may also be disposed at substantially the same planar orientation in cross-section. Each of wire electrodes 420 may breach barrel 402 once and may retain a gas-tight seal proximate the breach. Wire electrodes 420 can approach the center of gas chamber 406.

Either of wire electrodes 420 can be the discharge electrode depending on the connection to an oxygen conversion unit. The other electrode 420 can then function as the ground electrode. The ends of wire electrodes 420 situated within gas chamber 406 can form a sharp point. Alternatively, the ends of wire electrodes 420 can be blunt or a combination of one sharp end and one blunt end, respectively.

Electrical contact points 424 can be disposed on the outside of barrel 402, as well as various other positions, as will be readily recognized to one having ordinary skill in the art. Electrical contact points 424 can be disposed at approximately 180 degrees from each other on barrel 402. Electrical contact points 424 can be respectively connected with wire electrodes 420 and may be integral portions thereof.

Referring to FIGS. 5A-5F, syringe 500 can include barrel 502, plunger 504, gas chamber 506, plunger head 508, plunger shaft 510, plunger piston 512, tip portion 514, valve 516, connector 518, electrodes 520 and electrical contact points 524. Syringe 500 can be similar to syringe 400 of FIGS. 4A-4E in material aspects, including construction and operation. A difference can be that wire electrodes 520 can be angled. Electrodes 520 can be angled downwards proximate the inner bottom portion of barrel 502, thus, not strictly occupying substantially the same planar orientation in cross-section. As a result, the bottom portion of barrel 502 can be shaped so as to accommodate angled electrodes 520. For example, barrel 502 can be shaped to have a conical bottom portion. This configuration may further assist in preventing plunger piston 512 and electrodes 520 from contacting one another. Any further redundant description of like elements does not bear repeating here.

Referring to FIGS. 6A-6E, yet another syringe in accordance with at least one exemplary embodiment is shown. Similar to syringe 100 of FIGS. 1A-1E in construction and operation, syringe 600 can include barrel 602, plunger 604, gas chamber 606, plunger head 608, plunger shaft 610, plunger piston 612, tip portion 614, valve 616 and connector 618. A redundant of description of like elements does not bear repeating here.

Syringe 600 can include first and second foil electrodes 620. Foil electrodes 620 can be elongated and generally resembling strips in configuration. Foil electrodes 620 can be disposed on a portion of the inner wall of barrel 602. In at least one other exemplary embodiment, foil electrodes can be disposed on portions of the outer wall of barrel 602 (not shown). As shown, foil electrodes 620 can be disposed on opposing portions of the inner wall of barrel 602. A face of each of foil electrodes 620 can be in an opposing relationship. Also, foil electrodes 620 may vertically transverse a midportion of barrel 602.

As such, foil electrodes 620 can encompass an area of barrel 602 expected to contact plunger piston 612 of plunger 604 at certain times, when in use. The relatively thin nature of foil electrodes 620 can hinder or prevent non-beneficial interaction between the foil electrodes 620 and plunger piston 612.

Electrical contact surfaces/points 624 can be disposed on the outside of barrel 602, as well as various other positions, as will be readily recognized by one having ordinary skill in the art. As shown, electrical contact surfaces 624 can be situated on opposite side portions of barrel 602. Electrical contact surfaces 624 can be respectively connected to foil electrodes 620 and may be integral portions thereof. Electrical contact surfaces 624 can be narrower than the faces of foil electrodes 620. Electrical contact surfaces 624 can be thicker in diameter then the remainder of foil electrodes 620. Alternatively, foil electrodes 620 and electrical contact surfaces 624 can be of substantially the same width and/or thickness, both of which may vary.

Foil electrodes 620 can be one-piece inserts (e.g., molded inserts) having electrical contact surfaces 624. Foil electrodes 620 can breach barrel 602 so as to have a face on a portion of the inner wall of barrel 602 and the electrical contact surfaces 624 on the outside of barrel 602. Foil electrodes 620 can breach barrel 602 in a gas-tight manner.

Either of foil electrodes 620 can be the discharge electrode depending on the connection to an oxygen conversion unit. The other electrode 620 can then function as the ground electrode.

The disclosures of unpublished patent application Ser. Nos. 11/527,414 (Hooper) and 11/727,978 (Hooper, et al.) entitled "SYSTEM FOR DELIVERING OZONE" and "APPARATUS, METHOD AND SYSTEM FOR DELIVERING OXYGEN-OZONE", respectively, are incorporated by reference herein in their entireties. As will be recognized by one having ordinary skill in the art, syringes in accordance with at least one embodiment of the present disclosure can be suitably designed to functionally replace exemplary sterile vials (i.e. oxygen-ozone cells) of the '414 application for use with exemplary ozone conversion units as otherwise disclosed (and further described herein below), with or without ordinary modification, in the '414 application. Alternatively, conventional ozone generators, with or without ordinary modification, can be used to convert a portion of oxygen to ozone within syringes in accordance with embodiments of the present disclosure.

There may not be a need to remove excess ozone from an ozone generator because the amount of ozone needed (without substantial excess) can be produced directly in an exemplary syringe. An exemplary syringe adapted for direct cooperation with a medical ozone generator can decrease manufacturing costs by combining the functionality of an ozone cell (e.g., sterile vial) with a therapeutic delivery instrument (e.g., a conventional syringe). The relatively simple design of one or more of the exemplary syringes described above can also decrease manufacturing costs. Simplicity of design may also decrease leakage incidents.

Moreover, syringe embodiments can be suitably designed to functionally replace exemplary oxygen-ozone cells of the '978 application. Such embodiments can be filled with concentrated oxygen using exemplary apparatuses for concentrating oxygen from air as otherwise disclosed, with or without ordinary modification, in the '978 application. Alternatively, oxygen can be supplied to exemplary syringes by any other means known to one having ordinary skill in the art. As a couple non-limiting examples, medical grade oxygen can be supplied from supply tanks or hospital supply lines.

An exemplary ozone conversion unit may include an ozone UV measurement assembly, a data input mechanism such as a dial to allow the user to select a desired ozone concentration, and a data display to display input and output data such as desired concentrations and measurements. After a syringe according to at least one exemplary embodiment is engaged to the ozone conversion unit, an ozone concentration may be selected and power applied to effect corona discharge and the resultant conversion of oxygen to the selected concentration of ozone. An exemplary syringe may then be disengaged, thus allowing for therapeutic treatment. Embodiments may be employed in any of a variety of situations including, for example, the therapeutic treatment of humans or animals by way of injection.

The ozone conversion unit may be used to convert an amount of oxygen contained in an exemplary syringe to ozone by facilitating power. Ozone conversion unit may include a high voltage transformer. In an exemplary embodiment, the high voltage transformer may have a potential difference of about 3-25 kV. The high voltage transformer may be connected to a power source and to another set of electrical contact points. In another exemplary embodiment, electrical contact points may be arranged to reversibly interface with the electrical contacts of an exemplary syringe.

The ozone conversion unit may further include a dial, a UV measurement assembly and a data display. The UV measurement assembly may include components relating to measurements using UV absorption techniques, whereby a beam is passed through the ozone and oxygen mixture to be received by a detector. Such a beam may have a wavelength within a range on the UV spectrum known to those skilled in the art to be absorbed by ozone such as ranges UV-A, UV-B, and UV-C. In an exemplary embodiment, a beam having wavelengths of about 253.7 nm, within the bounds of the UV-C range, may be used. Also, in an exemplary embodiment, a mercury vapor lamp may be used to measure the concentration of ozone. An alternative exemplary embodiment may employ a UV light emitting diode or other instruments known to one having ordinary skill in UV absorption techniques. An exemplary detector may be a photodiode or other photo detecting instruments known to those having ordinary skill in the art. The dial may be used to regulate or input a desired ozone concentration. An exemplary therapeutically effective concentration of ozone is 6% or less by volume. An exemplary syringe may be constructed to be received by the ozone conversion unit in such a way that orients an exemplary syringe for successful UV measurement.

In an exemplary embodiment, the electrical contact points may be situated to interface with the interior of a receptacle formed in the ozone conversion unit that is capable of receiving an exemplary syringe. The UV measurement assembly may be arranged to orient a UV measurement beam axially through and along the receptacle to be received by a UV detector. In an alternative embodiment, the UV measurement assembly may be arranged to orient the UV measurement beam through receptacle transversely. A further exemplary embodiment may include a door to be closed upon or around an engaged exemplary syringe, thereby reducing ambient light from infiltrating the receptacle and interfering with UV detector.

The data display may be used to display measurement data collected by UV measurement assembly, indicate power status, or convey other relevant information such as input data or to confirm engagement of an exemplary syringe within the ozone conversion unit and operating pressures. The data display may be used to display any information or data that may be useful to one having ordinary skill in the art. The ozone conversion unit may be constructed to receive power, which can be made to pass through the high voltage transformer, and both sets of electrical contact points, thereby causing the corona discharge assembly to act upon the oxygen contained by an exemplary syringe and effect the selected concentration of ozone.

Optionally, the exemplary ozone conversion unit may also be constructed to detect nitrogen oxides (NOx). If an exemplary syringe is contaminated with nitrogen, for example, due to ingress of air from such causes as a leak within the syringe or improper functioning of a filling apparatus and system, then NOx will be produced by charging with the ozone conversion unit. Absorption techniques can be used to indirectly detect nitrogen ingress into the syringe prior to charging.

While nitrogen itself is optically transparent, $NO_x$ molecules, which will be created from the ionization of nitrogen and oxygen, absorb light at various frequencies between 227 and 550 nm. Many $NO_x$ bands overlap with that of ozone making it difficult to isolate these oxides. However, $NO_2$ has absorption bands (400-550 nm) that are distinct from ozone (253.7 nm) making it well suited to detect nitrogen ingress and formation of $NO_x$'s.

Also optionally, an exemplary ozone conversion unit or an exemplary syringe may be constructed to measure leaks within the syringe because at least one visual indicator or sensor for measuring changes in pressure known to those having ordinary skill in the art may be suitable placed for such a purpose. Moreover, the dielectric property of gases may provide another way to measure the amount of nitrogen potentially within the syringe. Oxygen and nitrogen have different dialectic constants and may be detected based on this difference.

The foregoing description and accompanying drawings illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A cell for producing an amount of ozone from oxygen, comprising:
    a syringe having a gas chamber;
    at least one electrode attached to the syringe; and
    at least one electrical contact point outside the gas chamber, the at least one electrical contact point connected to the at least one electrode, wherein the cell is configured to interface with an ozone generator;
    wherein the at least one electrode is a wire electrode at least partially within the gas chamber and;
    a foil electrode attached outside the syringe, the wire electrode extending towards and approaching a face of the foil electrode.

2. The cell of claim 1 wherein the at least one electrode and the at least one electrical contact point are integral.

3. An ozone generation system, comprising:
    a syringe having a gas chamber and at least one electrode connected to at least one electrical contact point
    wherein the at least one electrode is a wire electrode at least partially within the gas chamber and;
    a foil electrode attached outside the syringe, the wire electrode extending towards and approaching a face of the foil electrode; and
    a medical ozone generator connected to the syringe via the at least one electrical contact point.

* * * * *